United States Patent [19]

Walkowiak et al.

[11] 4,302,376
[45] Nov. 24, 1981

[54] DENTAL MATERIALS WHICH ARE OPAQUE TO X-RAYS AND ARE BASED ON ORGANIC PLASTICS IN PASTE FORM

[75] Inventors: Michael Walkowiak, Leverkusen; Wolfgang Podszun, Cologne; Bernhard Leusner, Leverkusen; Carlhans Süling, Odenthal; Hans H. Schulz, Leichlingen, all of Fed. Rep. of Germany

[73] Assignee: Bayer Aktiengesellschaft, Leverkusen, Fed. Rep. of Germany

[21] Appl. No.: 95,723

[22] Filed: Nov. 19, 1979

[30] Foreign Application Priority Data

Nov. 24, 1978 [DE] Fed. Rep. of Germany ....... 2850918

[51] Int. Cl.³ .............................................. A61K 6/08
[52] U.S. Cl. .............................. 260/29.7 UA; 106/35; 260/29.6 RB; 260/29.7 UP; 260/42.52; 525/4; 525/226; 525/228; 525/297; 525/308; 525/309

[58] Field of Search .................. 525/226, 228, 4, 308, 525/309, 297; 106/35; 260/29.7 UA, 29.7 UP, 29.6 RB, 42.52

[56] References Cited

U.S. PATENT DOCUMENTS 3,959,212 5/1976 Rockett et al. .................... 106/35
4,032,504 6/1977 Lee et al. ........................... 106/35

Primary Examiner—Harold D. Anderson
Attorney, Agent, or Firm—Sprung, Felfe, Horn, Lynch & Kramer

[57] ABSTRACT

The invention provides dental materials which are opaque to X-rays and are based on organic plastics in paste form, which comprises (a) a polymerizable binder, (b) a crosslinked bead polymer and (c) an X-ray contrast medium. The materials can also contain as an additional component (d) a fine-particled inorganic filler which is not opaque to X-rays. The materials are useful, inter alia, for filing dental cavities.

13 Claims, No Drawings

DENTAL MATERIALS WHICH ARE OPAQUE TO X-RAYS AND ARE BASED ON ORGANIC PLASTICS IN PASTE FORM

The present invention relates to novel X-ray opaque dental materials based on organic plastics.

The use of dental materials which are opaque to X-rays for the preparation of dental fillings is known. These materials, called composites, contain fine-particled glass powder as the filler which is opaque to X-rays. The disadvantage of these materials is that they cannot be polished and have all the known disadvantages resulting therefrom. Because of their consistency and tackiness, they also have other technological and clinical disadvantages.

The material is introduced into the cavity by wiping in, and, after filling the cavity, in many cases some of the composition introduced is stripped from the wall of the cavity due to adhesion to the filling instrument. This phenomenon cannot as a rule be detected by the dentist and thus leads to non-parietal incomplete fillings, with the known disadvantages of these.

The increased tackiness of the filling materials known hitherto has a particularly adverse effect in the case of multi-surface cavities. Thus, as is known from the amalgam filling technique, perfect filling of the cavity is only possible if a filling material is introduced in portions. In this filling technique, small portions are first pressed parietally into the angles of the cavity, and only then is the cavity filled. A corresponding procedure using the plastic materials hitherto known is not possible.

Whilst in the case of single-surface fillings in the region of the front of teeth the shape of the surface is achieved by applying moulding strips, the shaping of occlusal surfaces with materials which have a tacky consistency presents difficulties. Thus the areas of the masticating surfaces could be shaped only coarsely in the case of the materials known hitherto. Shaping by rotating abrasive and polishing instruments was thus usually required after hardening. As is known, damage to the adjacent enamel areas is as a rule unavoidable during this process. The results of this are distortions in the relief of the masticating surface and in some cases occlusal disturbances.

Attempts have been made to produce the desired shape of the surface by producing a "carvable" consistency. However, this "carvable" property only results when a certain degree of polymerisation has already been achieved. If the filling material is worked in this state, the filling surface can crack open or tear and thus damage to the filling cannot be excluded. These cracks, produced by "carving", can be openings for microorganisms and for dye-stuffs, with the known effects. Moreover, working of materials which are already partly polymerised can lead to interference with the polymerisation.

According to the present invention there is provided a dental material which is opaque to X-rays and is based on organic plastics in paste form, which comprises (a) a polymerisable binder, (b) a crosslinked polymer, (c) an X-ray contrast medium and, optionally (d) a fine-particled inorganic filler which is not opaque to X-rays.

It has been found, surprisingly, that these pastes are outstandingly suitable as a dental filling material.

The materials according to the invention can be prepared in a consistency which makes processing as is customary in the amalgam filling technique possible, that is to say they can be (A) pressed in and (B) shaped. The following remarks relate to aspect (a) of filling technique:

With the materials according to the invention, it is possible, using a non-tacky, firm consistency which is suitable for pressing in, to fill single-surface and multi-surface cavities parietally in several portions. The special property of the material means that there is no formation of layers when filling is effected in portions, that is to say the individual portions bond to one another homogeneously. After introduction of a particular portion into the cavity and the pressing-in or adapting thereof, this portion remains in position without changing its shape, that is to say it cannot even be deformed elastically.

Furthermore, because of the special consistency, the cavity can be filled using so-called amalgam guns without the filling material being pulled off again from the wall of the cavity or continuing to adhere to the nozzle of the gun.

The following remarks relate to aspect (b) of filling technique:

The materials according to the invention exhibit a consistency which allows shaping by instruments and is already obtained immediately after the mixing process. This consistency makes it possible for the occlusal individual form of the masticating surface to be shaped, after filling the cavity, by means of suitable instruments, for example of plastic or of metal, such as are used in the amalgam filling technique.

The paste-like dental materials, according to the invention, based on organic plastics, are transformed, by hardening, into solid substances. These substances have the great advantage that they are opaque to X-rays and can readily be polished.

For the preparation of the dental materials in accordance with the invention, from 18 to 60, and preferably from 25 to 50, parts by weight polymerizable binder, from 20 to 75, and preferably from 30 to 65, parts by weight crosslinked bead polymers, from 5 to 60, and preferably from 5 to 45, parts by weight X-ray contrastant, optionally up to 28 wt. % finely divided inorganic filler not opaque to X-rays, and from 0.01 to 5 parts by weight initiators are mixed to form a paste.

To facilitate paste preparation, inhibitors or light stabilizers may be added. For specific indications, it may be advisable to add also dyes.

Suitable polymerisable binders for the preparation of the dental materials according to the invention are the esters of methacrylic acid and monohydric and polyhydric alcohols, optionally mixed with other vinyl monomers. It is particularly favourable if the content of methacrylic acid esters is over 80%. It is also particularly favourable if the polymerisable binders comprise at least 50% by weight of esters of methacrylic acid with two or more polymerisable double bonds.

Examples of suitable esters of methacrylic acid which may be mentioned are aliphatic (particularly $C_1$–$C_4$-alkyl) and cycloaliphatic esters, (particularly $C_4$–$C_7$, especially $C_5$–$C_6$, cycloalkyl) such as methyl methacrylate, ethyl methacrylate and cyclohexyl methacrylate.

Very particularly suitable binders are furthermore esters of polyhydric alcohols with a molecular weight of 190–10,000, particularly esters of bivalent and trivalent alcohols with a molecular weight of 190–800, such as, for example, ethylene glycol dimethacrylate, triethylene glycol dimethyl methacrylate, neopentylglycol dimethacrylate or trimethylolpropane trimethyacrylate, and moreover urethane and ureidopolymethacrylates, which are accessible by reacting a hydroxylalkyl methacrylate or aminoalkyl methacrylates with polyisocyanates, for example the compound of the formula

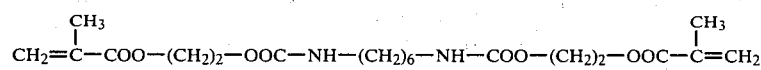

Very good pastes are obtained if at least a proportion of the binder used consists of compounds of the bis-GMA type, of the formula

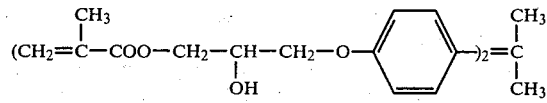

Dental filling compositions with a good consistency and a high level of mechanical strength are obtained, in particular, if mixtures of various methacrylic acid esters are used as the binder, for example mixtures of 20-70 parts of weight of bis-GMA and 80-30 parts of weight of triethyleneglycol-dimethylacrylate.

The crosslinked bead polymers employed for the preparation of the paste should consist of polymerised methacrylic acid esters, preferably methacrylic acid methyl ester, to the extent of more than 50% by weight. Suitable monomers having a crosslinking action are polyvinyl compounds which can be copolymerised with methyl methacrylate, such as, for example, ethylene glycol dimethacrylate or divinylbenzene, and the proportion of crosslinking agent should be 2 to 35% by weight of the monomer mixture. Beside the crosslinking agent, other monomers can be copolymerised in the bead polymer for example in order to influence the swelling properties of the bead polymer or to modify the mechanical properties of the hardened dental plastic. The average particle size of the bead polymers employed should be between 10 and 100$\mu$; the range from 10 to 70$\mu$ is particularly favourable.

Bead polymers as described in European patent specifications Ser. No. 79104246.8 and Ser. No. 79104253.4 are furthermore particularly suitable for the paste formulation. The use of bead polymers filled with inorganic fillers is particularly advantageous since dental materials in which both the bead polymer and the interstices between the beads equally contain inorganic filler, whereby a high degree of homogeneity in the hardened material is achieved.

Such polymers are bead polymers having a mean bead diameter of from 10 to 200$\mu$ of one or more polymerized viscous methacrylates and/or dimethacrylates having a viscosity of from 0.5 to 500 Pa.s and, optionally, up to 20% by weight of one or more other vinyl monomers are furthermore particularly suitable for the paste formulation.

Polymer beads having an average bead diameter of from 5 to 500$\mu$ consisting of an inorganic fine-particled filler and polymerized (meth)acrylic acid esters having a viscosity of from 0.1 to 10 Pa.s, are also particularly suitable for the paste formulation.

Any of the known standard X-ray contrast media can be used, for example solid, sparingly soluble heavy metal compounds, (particularly in the form of salts or oxides). Also included are organic iodine compounds used as X-ray contrast compounds, such as those disclosed in Kirk-Othmer "Encyclopedia of Chemical Technology," 2nd Ed., Vol. 17, pages 132-140 published by Interscience Publishers, New York, N.Y. (1968). They must be in a particularly finely divided form, preferably with an average particle size in the range of 1 m$\mu$-5$\mu$.

Barium compounds, for example barium sulphate, barium silicate and barium fluoride, are very particularly suitable. However, compounds of bismuth, for example bismuth oxynitrate, zirconium, for example zirconium dioxide, and lanthanum, for example lanthanum oxide and compounds of thorium and the rare earth metals are also suitable. Inorganic and organic iodine compounds can furthermore be used as the X-ray contrast medium.

The amount of X-ray contrast medium employed can be varied within wide limits, depending on the clinical requirements. A good X-ray contrast is achieved, for example, with a content of 15-40, preferably 20-30 parts of weight of BaSO$_4$.

Suitable fine-particled inorganic fillers which are not opaque to X-rays, for the dental materials according to the invention are, above all, silicon dioxide, aluminium dioxide, silicates and silicate glasses, as long as their average particle size is within the range of 1 m$\mu$-1$\mu$. It is particularly favorable to use amorphous silicon dioxide which is obtained by flame pyrolysis, and in particular amorphous silicon dioxide with a primary particle size of 5-30 m$\mu$ and a specific surface area, measured by the BET method, of 40-400 m$^2$/g.

The fine-particled inorganic filler can be after-treated with silane adhesion promoters, for example with vinyltrimethoxysilane or with trimethoxy-(3-methacryloxyloxypropyl)-silane, in order to improve the bond between the inorganic filler and the organic matrix, but this after-treatment step is not absolutely necessary for the preparation of the dental materials according to the invention.

Particularly preferred dental materials according to the present invention are those in which the proportion of crosslinked bead polymers, X-ray contrast medium and inorganic filler, if any, is 51 to 82% by weight. Further preferred dental materials are those in which the proportion of X-ray contrast medium is 5 to 45% by weight. Yet further preferred dental materials are those in which the proportion of additional inorganic filler is up to 28% by weight.

The customary starter system can be used for hardening the dental materials according to the invention, that is to say systems which supply free radicals, anions or cations and which can trigger off free radical, anionic or cationic polymerization. Peroxides or aliphatic azo compounds are particularly suitable in the case of systems which supply free radicals, for example, benzoyl peroxide, lauroyl peroxide or azoisobutyric acid dinitrile, which normally are used in amounts ranging from 0.1 to 5 wt. %. While the cure at elevated temperature is carried out with the aid of peroxides or other radical initiators alone, curing at room temperature requires the addition of accelerators, preferably aromatic amines. Suitable accelerators are N-N substituted toluidines and xylidines, such as NN-dimethyl-p-toluidine or NN-bis (2-hydroxyethyl)exylidine. A good cure is obtained with an 0.5 to 3% amine addition. An advantageous form for a peroxide/accelerator-activated system is the two-paste form, one of the pastes incorporating the radical initiator and the other the accelerator, and curing being initiated by mixing of the two pastes.

Curing by means of UV light or visible light, with appropriate sensitization, is also a very good method. Suitable photoinitiators are, for example, benzophenone and its derivatives, benzoin and its derivatives such as benzoin ether, anthraquinone, and aromatic disulfides.

EXAMPLE 1

Preparation of a bead polymer from methyl methacrylate, ethylene glycol dimethacrylate and ethyl acrylate

Polymerisation

Reaction vessel: 6 liter autoclave with a double-anchor stirrer

Solution I: 2,500 ml of distilled water (Dispersing agent solution: 500 ml of a 7.5% strength aqueous solution of the copolymer of 1 part by weight of methacrylic acid and 1 part by weight of methyl methacrylate, with a pH of 6 and a viscosity of 3,650 cp.)

Solution II: 765 g of methyl methacrylate, 90 g of ethyl acrylate, 45 g of ethylene glycol dimethacrylate, 4.5 g of benzoyl peroxide and 4.5 g of lauroyl peroxide.

Solution I is initially introduced into the autoclave and is stirred for 5 minutes. Solution II is added all at once, with the stirrer stopped, and the autoclave is flushed with nitrogen. The pressure is then increased to 5 bars of nitrogen, the stirrer speed is adjusted to 400 rpm and the mixture is heated to 80° C. When the exothermic reaction starts, the mixture is cooled to an extent such that the temperature remains below 90° C. The mixture is subsequently stirred at 80° C. for 2 hours.

Working up

The mixture is let down and diluted to 10 l with distilled water. After adding 180 g of glacial acetic acid, it is heated to 90°–100° C. for 15 minutes. The bead polymer which precipitates is filtered off after cooling, washed by stirring three times in 5 l of distilled water at a time, and dried at 60° C.

Yield: 845 g

Average bead diameter: 25μ.

EXAMPLE 2

Preparation of a bead polymer filled with Ba SO$_4$

The same reaction vessel and the same dispersing agent solution as in Example 1 are used.

Solution III 220 g of methyl methacrylate, 30 g of ethyleneglycol dimethacrylate, 50 g of polymethyl methacrylate ($[\eta]=1.05$, in chloroform) and 100 g of barium sulphate (Riedel de Haën AG)

The components of solution III are introduced into the reaction vessel with exclusion of atmospheric oxygen and are stirred at room temperature until the polymer has dissolved. 1.1 g of benzoyl peroxide is added to the resulting mixture and the mixture is stirred for a further 15 minutes. Solution I (dispersing agent solution) is then added all at once and the stirring speed is increased to 400 rpm.

The suspension formed is heated to 80° C., and when the exothermic reaction starts it is cooled to an extent such that the temperature is kept below 85° C. When the reaction has subsided, the mixture is kept at 85° C. for 2 hours, whilst further stirring. Working up is carried out as in Example 1.

Yield: 275 g, Ba SO$_4$ content: 28.8%, average particle diameter: about 45μ.

EXAMPLE 3

Paste-like dental material according to the invention (A) Peroxide paste 140 g of the bead polymer from Example 1, 42 g of silanised amorphous silicon dioxide (surface area, measured by the BET method, 170 m$^2$/g), 116 g of barium sulphate, 102 g of urethane dimethacrylate (reaction product of 2,2,4-trimethylhexamethylene diisocyanate and 2-hydroxyethyl methacrylate, stabilised with 200 ppm of HQME (Plex 6661 from Messrs. Röhm GmbH Darmstadt said HQME being hydroxyquinone monomethyl ether) and 2.5 g of benzoyl peroxide.

The individual components are put into a kneader and kneaded intensively for 60 minutes, a vacuum of about 20 mm Hg being applied during the last 10 minutes. A kneadable mass with a particularly firm consistency is obtained in this manner.

(B) Amine paste

The bead polymer, amorphous silicon dioxide, barium sulphate and urethane dimethyacrylate are employed in the same amounts as in the case of the peroxide paste and are processed. Instead of the peroxide, 1.2 g of N,N-bis- (2-hydroxypropyl)-3,5-dimethylaniline are employed.

(C) Paste-like composition for filling teeth

Equal parts (for example 200 mg each ) of the amine paste and peroxide paste are mixed intensively for 30 seconds. The resulting mixture is outstandingly suitable as a dental filling material. It hardens in a few minutes with little shrinkage on polymerisation.

EXAMPLE 4

Paste-like dental material according to the invention

An amine paste and a peroxide paste are prepared from, in each case, 105 g of the bead polymer according to Example 2, 10 g of silanised amorphous silicon dioxide (surface area, measured by the BET method, 170 m$^2$/g), 26 g of barium sulphate, 42 g of bis-GMA (Nupol 46-4005 from Messrs. Freeman Chemical) and 22 g of triethylene glycol dimethacrylate, using 1.1 g of benzoyl peroxide or 0.9 g of N,N-bis-(2-hydroxypropyl)-3,5-dimethylaniline, by a procedure corresponding to that in Example 3.

This material is mixed like the material from Example 3. A mixture which is outstandingly suitable as a dental filling material is likewise obtained.

EXAMPLE 5

Pasty dental material in accordance with the invention

A pasty mixture is prepared by the procedure set forth in Example 3 from 200 g bead polymer according to Example 1, 80 g barium sulfate, 120 g bis-GMA, 80 g triethylene glycol dimethacrylate, and 4 g benzoin isopropyl ether.

This material is extremely well suited for use as a dental filling material. It will cure when exposed to UV light (Uviolite lamp of the Espe company) within 40 sec in layers 2.5 mm thick.

What is claimed is:

1. A dental paste opaque to X-rays, consisting essentially of (a) at least one ester of methacrylic acid and a monohydric or polyhydric alcohol as polymerizable binder, (b) at least one crosslinked bead polymer plastic made from an ester of methacrylic acid and a monohydric or polyhydric alcohol, and (c) an X-ray contrast medium.

2. The paste according to claim 1 further containing a fine-particled inorganic filler which is not opaque to X-rays.

3. The paste according to claim 1 or 2 wherein the polymerizable binder is present in an amount more than 80% by weight based on the weight of at least one aliphatic or cycloaliphatic ester of methacrylic acid.

4. The paste according to claim 1, wherein the polymerisable binder contains at least 50% by weight, based on the total weight of binder, of an ester of methacrylic acid having at least two ethylenically unsaturated double bonds.

5. A dental material according to claim 1, in which the polymerisable binder is a mixture of methacrylic acid aliphatic or cycloaliphatic esters.

6. The paste according to claim 1, wherein the bead polymer is made from monomers comprising more than 50% by weight, based on the total weight of bead polymer, of one or more esters of methacrylic acid.

7. A dental paste according to claim 1, in which the crosslinked bead polymer has an average particle size of 10 to 100μ.

8. A dental paste according to claim 1, in which the X-ray contrast medium is a solid, sparingly soluble inorganic substance with an average particle size of 1 mμ–5μ.

9. A dental paste according to claim 2, in which the additional fine-particle inorganic filler has an average particle size of 1 mμ–1μ.

10. A dental paste according to claim 2, in which the additional fine-particled inorganic filler consists of amorphous silicon dioxide.

11. A dental material according to claim 2, in which the proportion of additional inorganic filler is up to 28% by weight of said inorganic filler.

12. A dental material according to claim 2, in which the proportion of crosslinked bead polymer, X-ray contrast medium and inorganic filler, together is 51 to 82% by weight of said inorganic filler.

13. A dental material according to claim 1, in which the proportion of X-ray contrast medium is 5 to 45% by weight of said dental paste.

* * * * *